United States Patent [19]

Howansky

[11] Patent Number: 5,292,334
[45] Date of Patent: Mar. 8, 1994

[54] SURGICAL FASTENER

[75] Inventor: Steven Howansky, Wilton, Conn.

[73] Assignee: United States Surgical Corporation, Norwalk, Conn.

[21] Appl. No.: 41,010

[22] Filed: Mar. 31, 1993

[51] Int. Cl.$^5$ .............................................. A61B 17/00
[52] U.S. Cl. .................................................. 606/220
[58] Field of Search ......................... 606/219, 220, 75; 411/457

[56] References Cited

U.S. PATENT DOCUMENTS

| | | |
|---|---|---|
| D. 280,931 | 10/1985 | Green . |
| D. 280,932 | 10/1985 | Green . |
| D. 286,180 | 10/1986 | Korthoff . |
| D. 286,441 | 10/1986 | Korthoff et al. . |
| D. 286,442 | 10/1986 | Korthoff et al. . |
| 2,881,762 | 4/1959 | Lowrie . |
| 3,357,296 | 12/1967 | Lefever . |
| 4,060,089 | 11/1977 | Noiles . |
| 4,402,445 | 9/1983 | Green . |
| 4,523,591 | 6/1985 | Kaplan et al. . |
| 4,534,352 | 8/1985 | Korthoff . |
| 4,610,250 | 9/1986 | Green . |
| 4,667,674 | 5/1987 | Korthoff et al. . |
| 4,724,839 | 2/1988 | Bedi et al. ............................ 606/220 |
| 4,728,020 | 3/1988 | Green et al. . |
| 4,932,960 | 6/1990 | Green et al. . |

FOREIGN PATENT DOCUMENTS

| | | |
|---|---|---|
| 0129442 | 12/1984 | European Pat. Off. . |
| 0202090 | 11/1986 | European Pat. Off. . |
| 0315344 | 5/1989 | European Pat. Off. . |

Primary Examiner—Stephen C. Pellegrino
Assistant Examiner—Gary Jackson

[57] ABSTRACT

A surgical fastener comprising a fastener member and a retainer member is disclosed. The fastener member comprises a base and a pair of substantially parallel prongs extending substantially perpendicularly from the base in substantially the same direction, each prong being spaced inward from its respective end of the base, and having a prong tip configuration that allows for improved tissue penetration and thereby minimizes splaying of the prongs. Preferably, the base is the same length as the retainer member. Preferably, the prongs are substantially equidistant from the transverse centerline of the base. Also in accordance with this invention is a surgical fastener having a prong tip which maintains its improved ability to penetrate tissue after annealing of the surgical fastener.

13 Claims, 7 Drawing Sheets

SURGICAL FASTENER

BACKGROUND OF THE INVENTION

This invention relates to surgical fastener for fastening body tissue, and more particularly to a fastener having improved tip structures for better penetration of the tissue to be fastened. This invention also relates to an improved tip which retains good penetration characteristics even after shrinkage due to annealing of the fastener. Additionally, an improved fastener with a trocar tip is disclosed.

Surgical fastening devices allow a surgeon to fasten body tissue by applying surgical fasteners. The fasteners, usually arrayed in rows, may be applied sequentially or simultaneously depending on the type of fastener applying instrument and the requirements of the surgical procedure. Surgical fasteners are often made of inert metals such as titanium and stainless steel. Metal fasteners are generally U-shaped staples, the legs of which are crimped for fastener closure when the staple is driven through the body tissue and into an anvil with staple crimping depressions.

Non-metallic fasteners are also known and may be preferable to metal fasteners in some procedures. Non-metallic fasteners may be made of polymeric material, and preferably bioabsorbable synthetic polymers. Bioabsorbable polymers offer a significant advantage in that they remain in the body tissue only as long as is necessary for tissue healing. After that the bioabsorbable fastener gradually degrades. A separate procedure for its removal is not required.

Polymeric materials generally do not possess the strength and ductility of metals. Hence, closure of the polymeric fasteners is achieved without crimping the fastener structure. Typically, polymeric fasteners are fabricated as two-part structures: a generally U-shaped fastener portion, and a corresponding retainer portion which engages and interlocks with the legs of the fastener portion. The legs or prongs of the fastener member are driven through one side of the tissue to be fastened and the retainer member interlocks with the prongs of the fastener member on the other side of the tissue to hold the entire fastener structure in place.

Surgical fasteners and fastener applying apparatus are disclosed in U.S. Pat. Nos. 4,060,089; 4,402,445; 4,534,352; 4,610,250; 4,667,674; 4,728,020; 4,932,960; Des. 280,931; Des. 280,932; Des. 286,180; Des. 286,441; and Des. 286,442, all of which are herein incorporated by reference.

A frequent goal in fastening tissue is achieving hemostasis along the fastener line. Hemostasis is achieved by exerting pressure on the tissue from both sides. If metal staples are used, that pressure (hereinafter referred to as "hemostatic pressure") is exerted by and between the base of the staple on one side of the tissue and the crimped legs on the other side of the tissue. In typical crimped metal staples no part of the staple extends beyond the ends of the base. Therefore, a second staple can be applied very close to the first staple, so that the bases of the two staples are in a line. In that case the gap between staples can be quite small so that hemostatic pressure is applied uniformly along the entire staple line.

In contrast, when two-part polymeric fasteners are used, hemostatic pressure is exerted by and between the retainer member and the backspan or crosspiece of the fastener member. In known two-part polymeric fasteners the prongs of the fastener member extend from the ends of the backspan. The retainer member is typically longer than the distance between the prongs and, therefore, must extend beyond the fastener member backspan. Accordingly, the backspans of adjacent fastener members lying in a line are separated by at least the sum of the distances by which adjacent retainer members extend beyond the associated fastener member backspans. Thus, there are gaps between adjacent fastener members. Full hemostatic pressure is not exerted on the tissue in these gaps.

One way to make up for the above-mentioned gaps in a line of polymeric fasteners is to provide fasteners with a crosspiece which extends beyond the span of the prongs so that the fasteners can be applied nearly touching each other such as disclosed, for example, in Korthoff et al., U.S. Pat. No. 4,667,674, issued May 26, 1987. Another way to make up for the above-mentioned gaps in a line of polymeric fasteners is to apply the fasteners in two parallel rows, with a linear offset between the rows so that the gaps in one row are opposite the bases of the fastener members of the other row.

U.S. Pat. No. 4,932,960 to Green et al. discloses a bioabsorbable two-part fastener having a fastener portion and a retainer. The fastener portion includes a locking surface oriented in the direction of the lengthwise extension of the fastener backspan, therein designated as an "X direction".

To facilitate the placement of multiple rows of fasteners it is desirable to have fasteners which are as narrow as possible. However, the narrower one makes a fastener of any given length and shape the weaker it is because there is simply less structural material. For this reason, the structural features of surgical fasteners which compensate for the lack of material by distributing or reducing stress become increasingly important as the fastener size is reduced.

In particular, stresses are created when the fastener portion is driven through body tissue. The fastener member prongs may tend to splay or spread apart as the prongs are forced through the tissue. Since the prongs must be precisely aligned and spaced apart in order to engage the corresponding apertures in the retainer portion, deformation of the prongs can cause failure of the faster and retainer portions to lock together, thereby resulting in bleeding from the loss of hemostasis and tissue holding.

SUMMARY OF THE INVENTION

A surgical fastener is provided herein which comprises a generally U-shaped fastener member including (i) a backspan, the lengthwise extent of which defines an X direction, (ii) at least two substantially parallel prongs extending substantially perpendicularly from the backspan and each having a tip portion terminating in a point for piercing body tissue, the lengthwise extent of the prongs defining a Y direction, the fastener member having at least one surface defining a Z direction which is transverse to both of the X and Y directions, the fastener member having at least two cutting edges located on the tip portions of the prongs and aligned in the X direction, and each prong having at least one locking surface extending from the prong in the Z direction. The fastener is preferably a two-part fastener and may include a retainer portion having (i) a base, and (ii) at least two columnar members attached to said base, each columnar member having an aperture to receive and retain the tip portion of a respective one of the prongs, and locking means to engage the locking surface.

In an alternative embodiment, the U-shaped surgical fastener member comprises (i) a backspan, the lengthwise extent of which defines X direction, (ii) at least two substantially parallel prongs extending substantially perpendicularly from the backspan and each having a tip portion terminating in a point for piercing body tissue, the lengthwise extent of the prongs defining a Y direction, the fastener member having at least one surface defining a Z direction which is transverse to both of said X and Y directions, the tip portions of the prongs each having a first triangular surface facing generally outward of the fastener member in the X direction, the apex of the first triangular surface being spaced apart from said terminal point of the prong tip by a cutting edge extending therebetween.

BRIEF DESCRIPTION OF THE DRAWINGS

Advantages of the present invention will be more apparent after consideration of the accompanying drawings in which like parts are indicated by like reference characters throughout and in which.

DETAILED DESCRIPTION OF PREFERRED EMBODIMENT(S)

An instrument for applying the surgical fasteners of the present invention is disclosed in U.S. Pat. No. 4,728,020 to Green et al. issued Mar. 1, 1988, herein incorporated by reference.

It should be understood that dimensions given in this specification (i.e, dimensions as to length, width, curvature, etc.) are for purposes of exemplification and are not to be construed as limitations on the invention. Any dimensions suitable for the purpose of fastening body tissue are contemplated as being within the scope of the invention.

The fasteners of the present invention may be fabricated from any biocompatible material suitable for the purpose of fastening body tissue. The material may or may not be bioabsorbable. However, preferred materials of fabrication are bioabsorbable polymers such as homopolymers and copolymers of glycolide, lactide, caprolactone, trimethylene carbonate, p-dioxanone, and mixtures thereof. A preferred polymeric material, which is absorbable in the body, is disclosed in Kaplan et al., U.S. Pat. No. 4, 523,591, issued Jun. 18, 1985, and herein incorporated by reference.

Figure 1A:
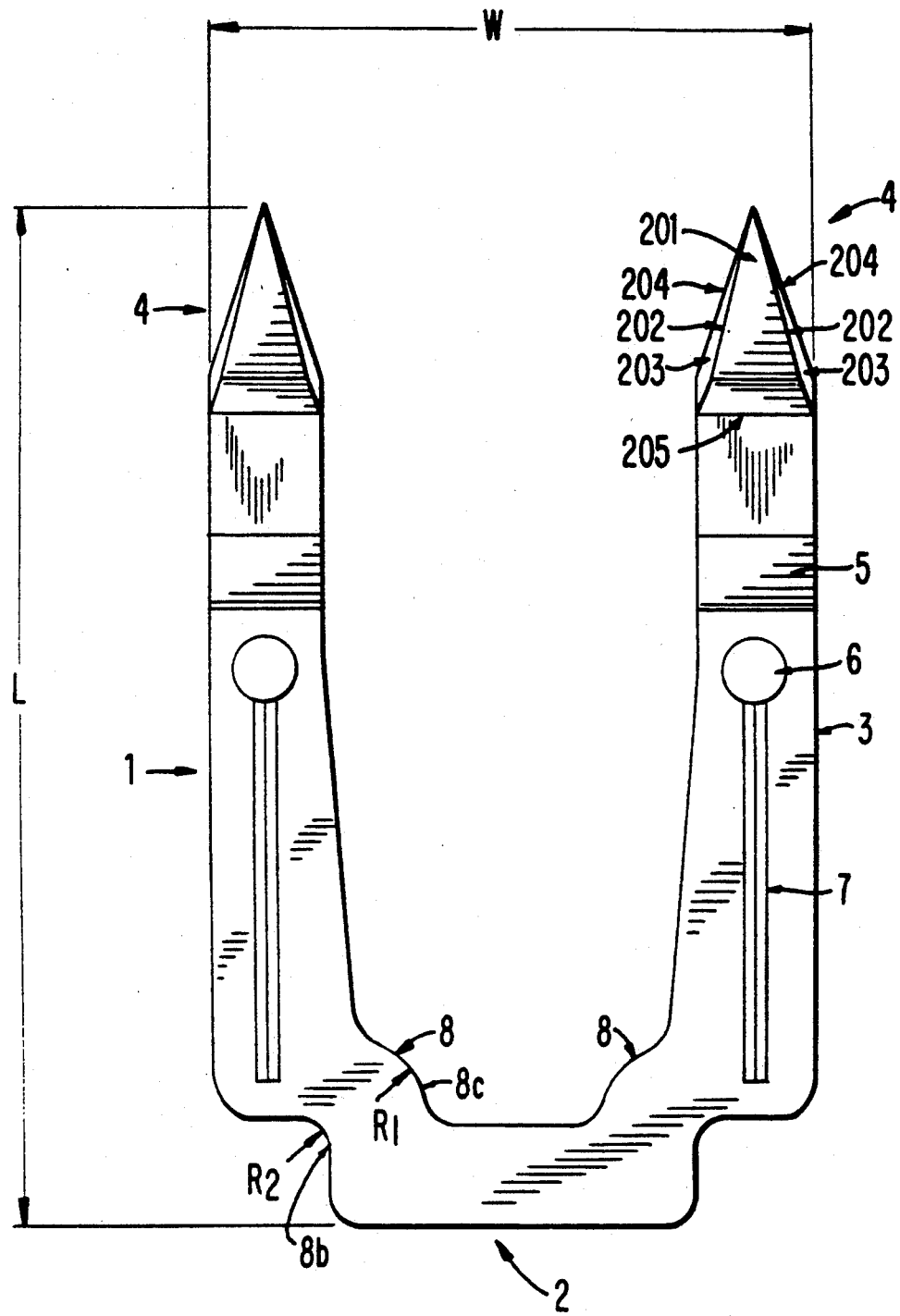
FIG. 1a is an elevational view of one embodiment of a surgical fastener member of the present invention.
Figure 1B:
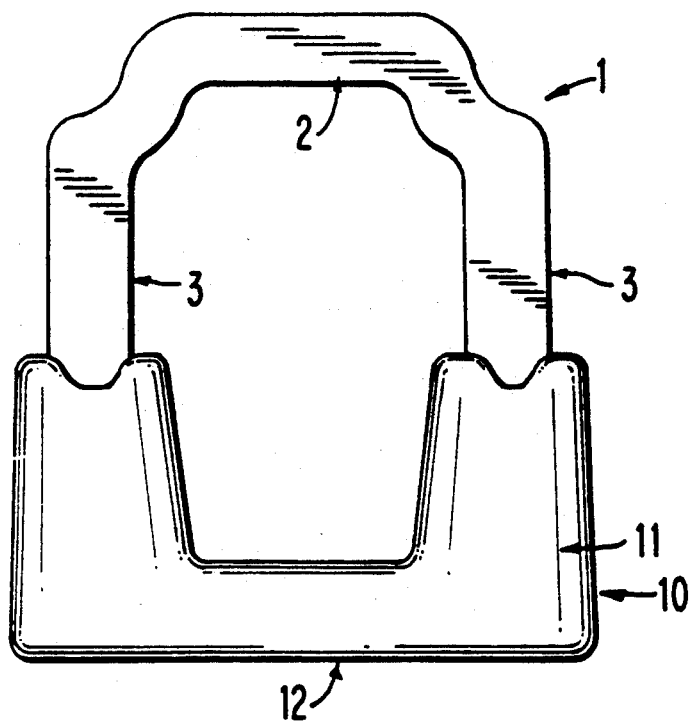
FIG. 1b is an elevational view diagrammatically illustrating the fastener member in conjunction with a retainer piece.
Figure 1C:
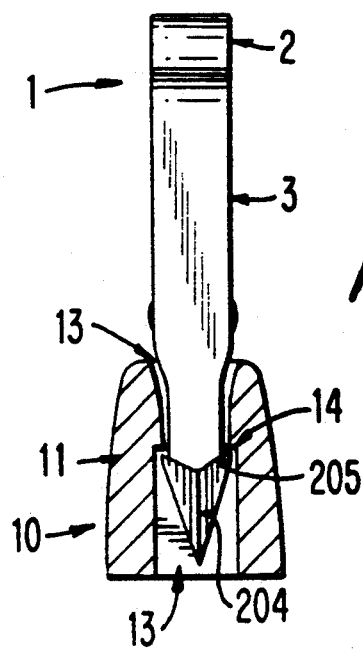
FIG. 1c is a partly sectional side view showing the fastener portion locked in a retainer piece.

Referring to FIGS. 1a, 1b, and 1c, surgical fastener member 1 includes two prongs 3 extending from backspan 2, each with a tip portion 4. The fastener preferably includes curved transition portions 8 between prongs 3 and backspan 2. The fastener preferably includes inclined portion 5, raised buttons 6 to provide frictional interference with the slot of the fastener applying instrument from which the fastener is driven, and guide ridges 7 to facilitate alignment of the fastener as it is being applied.

The fastener may be fabricated in any dimension suitable for the purposes described herein. In a preferred embodiment the overall length L of the fastener can be from about 0.285 inches to about 0.295 inches. The overall width W of the fastener can be from about 0.170 to about 0.175 inches. The inner curved surface $8a$ preferably can have a radius of curvature R, of from about 0.023 to about 0.027 inches. The outer curved surface $8b$ preferably can have a radius of curvature $R_2$ of from about 0.008 inches to about 0.012 inches.

In use the surgical fastener member 1 would extend through the tissue to be sutured and, as diagrammatically illustrated in FIGS. 1b and 1c, locked in a retainer portion 5. The retainer portion comprises two upright columnar members 11 extending from base 12, each columnar member having an aperture 13 for receiving and engaging a corresponding tip portion 4 of the fastener. Preferably, a locking ridge 14 is included in the retainer to cooperate with locking surface 205 of the fastener tip 4 to snap lock the fastener portion 1 and retainer portion 10 together when they are joined.

Figure 2:
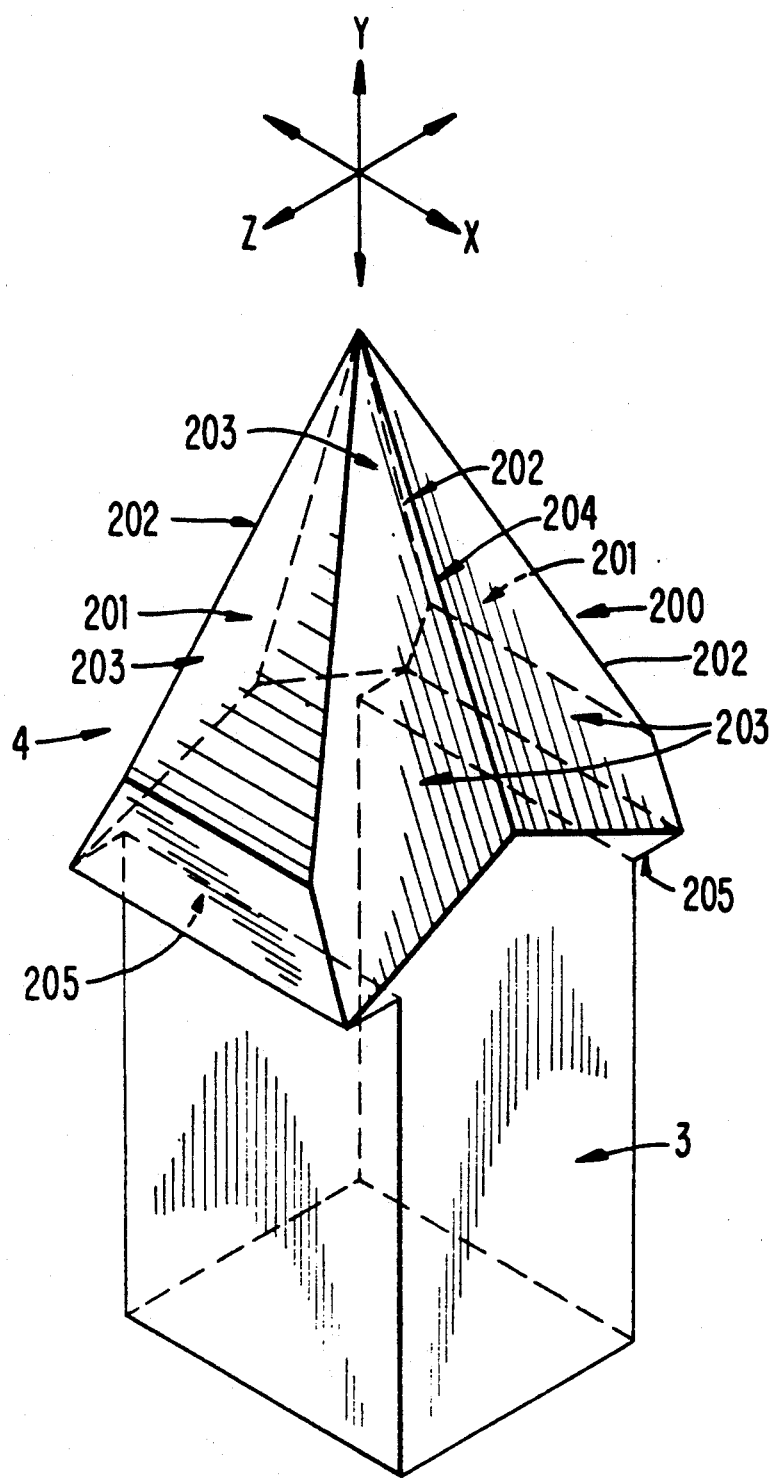
FIG. 2 is a fragmentary isometric view of a surgical fastener member having a tip with improved tissue penetration.

When fastener member 1 is applied to tissue, improved penetration of the tissue and resistance to splaying is realized by the shape of the tip portions. One preferred embodiment is shown in FIG. 2 where tip 4, extending from prong 3, has two opposing triangular tapered faces 201, having four cutting edges 202, two pairs of opposing tapered faces 203 formed by the slightly raised cutting edge 204, and the cutting edges 202, and a locking means 205 for locking into the surgical fastener retainer after penetrating the tissue. A two-part fastener/retainer combination is illustrated in U.S. Pat. No. 4,932,960.

The locking surface 205 is located on the side of prong 3 transverse to the side on which raised cutting edge 204 is located. Thus, if one defines coordinate axes as shown in FIG. 2 with the Y-axis extending along the length of the prongs 3, the x-axis extending along the length of the backspan 2, and the Z-axis extending transverse to both the X and Y axes, the raised edges 204 will be located on the inner and outer sides of prong tips 4 and are oriented along the X-axis direction. The locking surfaces 205, on the other hand, are oriented in the Z-axis direction, i.e., the locking surfaces 205 project outwardly from the prongs on the sides of the prongs which are transverse to the sides from which cutting edges 204 project. The configuration of the present invention provides increased strength while maintaining excellent performance with respect to tissue penetration and secure locking of the two-part fastener upon joining thereof.

Figure 3:
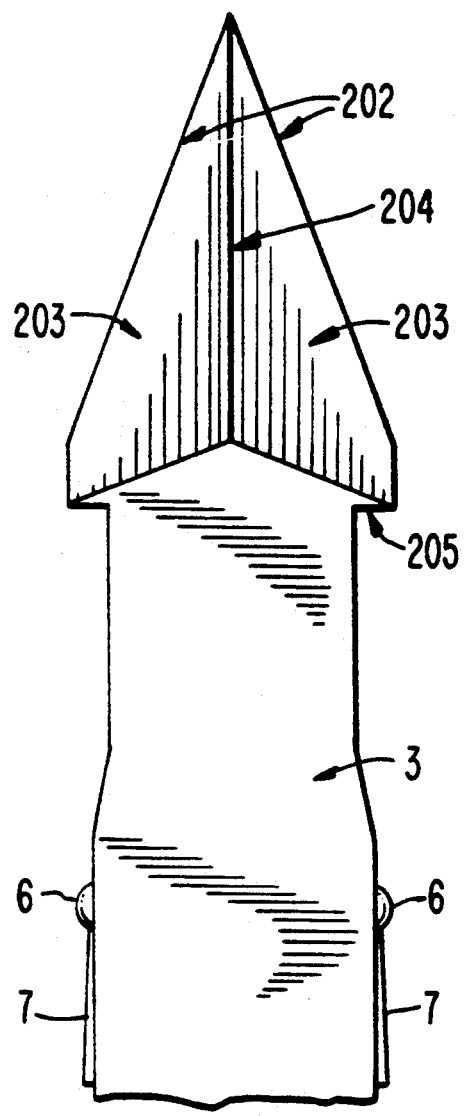
FIG. 3 is a fragmentary elevational view of the surgical fastener member of FIG. 2.

FIG. 3 shows another view of tip 4, where the two pairs of opposing tapered faces are defined by the cutting edges 202, the slightly raised cutting edge 204, the locking means 205 and prong 3.

Figure 4:
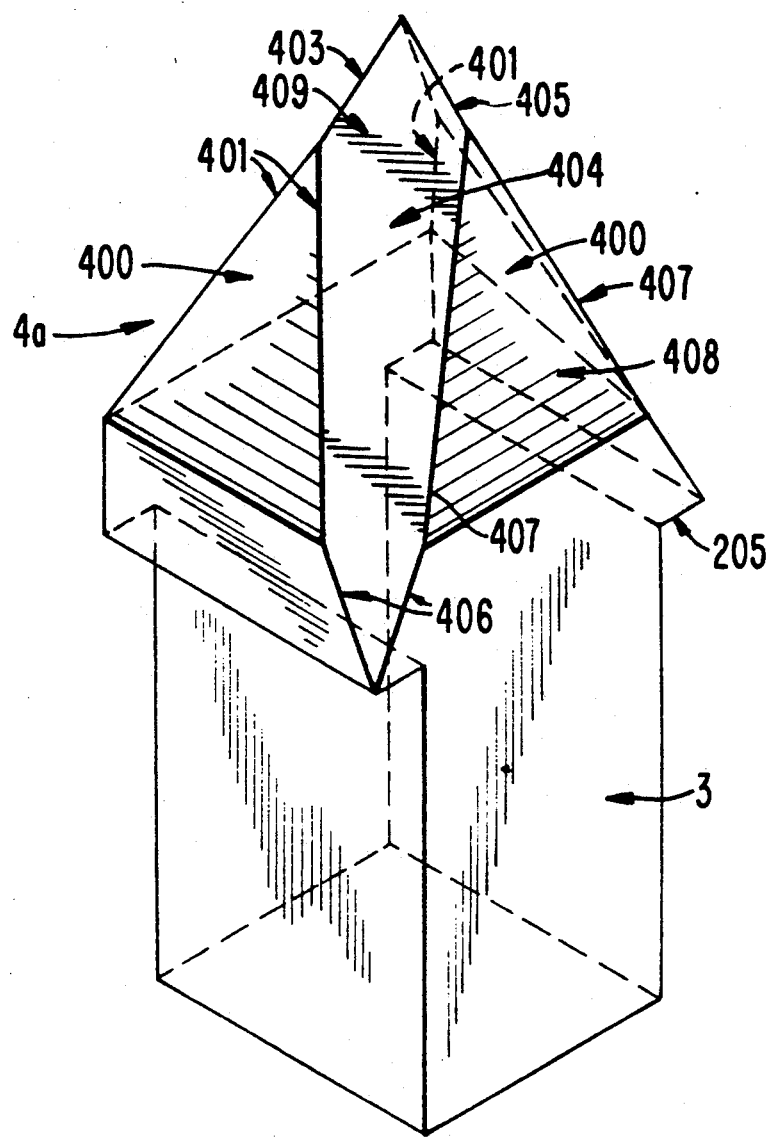
FIG. 4 is a fragmentary isometric view of a surgical fastener member having a trocar tip with improved tissue penetration.

Another embodiment of the invention is shown in FIG. 4, hereinafter referred to as a "trocar tip". FIG. 4 comprises a trocar tip 4a, extending from prong 3, having two opposing triangular tapered faces 400, forming four cutting edges 401, one pentagonal face 409, bounded by prong 3, cutting edges 401 and cutting edges 403, opposed by two hexagonal tapered faces 404, bounded by cutting edges 401, 403, 405, 406 and 407, and triangular tapered face 408, positioned between the hexagonal tapered faces 404 and bounded by cutting edges 407, and prong 3, and a locking means 205.

Figure 5:
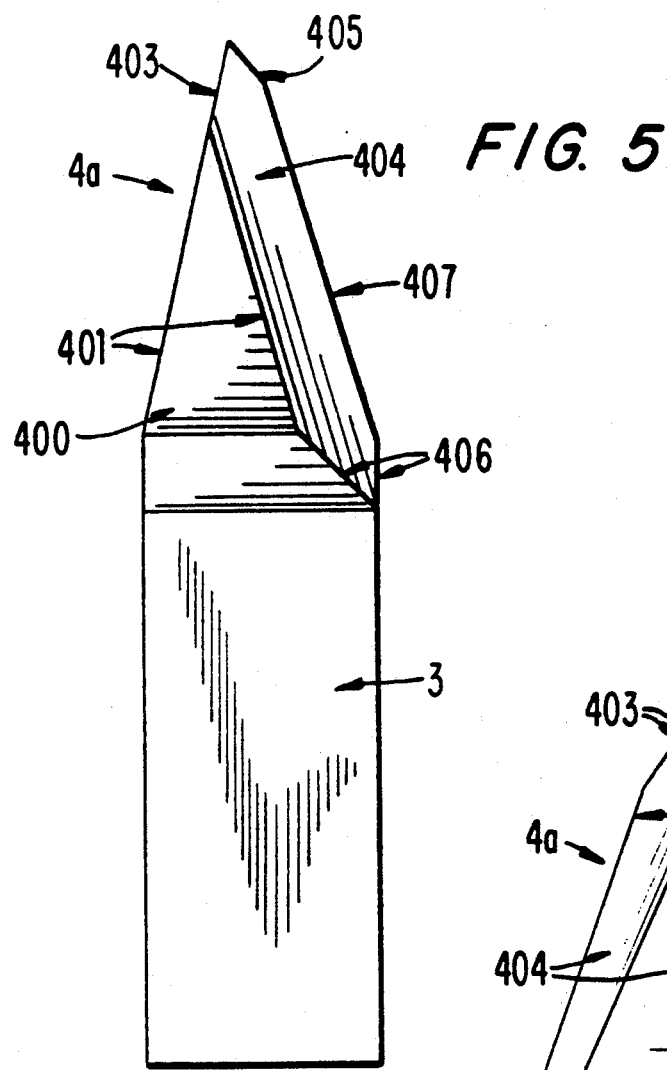
FIG. 5 is a fragmentary elevational view of the surgical fastener member of FIG. 4.

FIG. 5 shows trocar tip 4a, where triangular tapered face 400, and hexagonal tapered face 404, having cutting edges 401, and cutting edges 401, 403, 405, 406 and 407, respectively.

Figure 6:
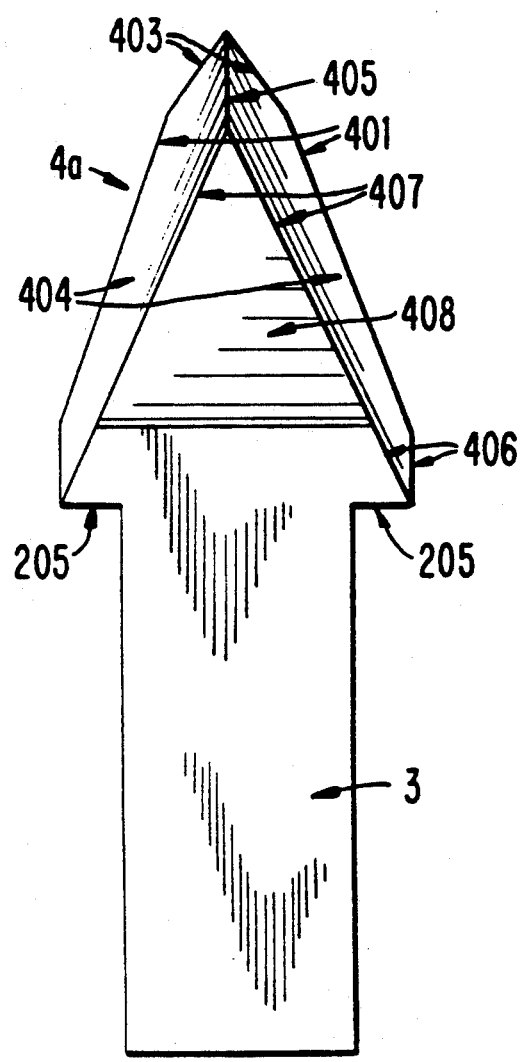
FIG. 6 is a fragmentary elevational view of the surgical fastener member of FIG. 4 rotated 90° from the view in FIG. 5.

FIG. 6 shows another view of trocar tip 4a, rotated 90° from that of FIG. 5, where triangular tapered face 408 and hexagonal tapered faces 404, having cutting edges 407, and cutting edges 401, 403, 405, 406 and 407, respectively.

The improved surgical fastener tips shown in FIGS. 2-6 provide improved tissue penetration with reduced tendency for splaying of the surgical fastener prongs as they are driven through the tissue and into the retainer, thereby providing the necessary hemostasis. The surgical fastener may be applied by various conventional fastener-applying apparatus which are known in the art.

Figure 7:
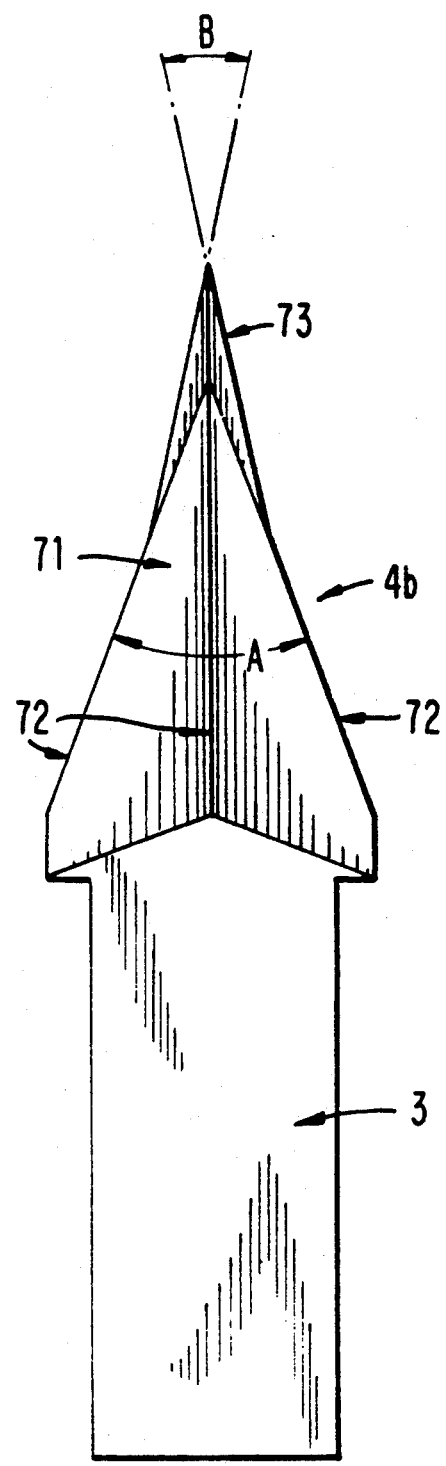
FIG. 7 is a fragmentary elevational view of a surgical fastener member having a tip with improved tissue penetration after annealing.

There is a tendency for shrinkage of the tip sections of the surgical fastener when it is annealed in the manufacturing process. This shrinkage can change the shape of the tip of the fastener such that penetration of tissue may be adversely affected. It has now been found that this adverse penetration ability of the surgical fastener tip may be overcome by the addition of an elongated point on the tip sections of the surgical fasteners during manufacture. One embodiment of this advantageous elongated point is shown in FIG. 7, where tip 4b, extending from prong 3, and having tapered faces 71, and cutting edges 72, has an elongated point 73, extending from the tip 4b, distal to prong 3. Angle B of the elongated tip 73 may be from about 29° to about 33+. Angle A of tip 4b may be from about 34° to about 37°. Thus tip 73 will possess a sharper angle than tip 4b for easier penetration of body tissue. It will be appreciated by those skilled in the art that the use of an elongated point or tip configuration is independent and that it may be utilized on any surgical fastener tip design with similar advantageous results.

One skilled in the art will recognize that the inventive principles disclosed herein can be practiced in other than the embodiments described, and the invention is not limited by those embodiments but only by the claims which follow.

What is claimed is:

1. A surgical fastener comprising:
   a) a generally U-shaped fastener member including
      (i) a backspan, the lengthwise extent of which defines an X direction,
      (ii) at least two substantially parallel prongs extending substantially perpendicularly from said backspan and each having a tip portion terminating in a point for piercing body tissue, the lengthwise extent of said prongs defining a Y direction, said fastener member having at least one surface defining a Z direction which is transverse to both of said X and Y directions, said fastener member having at least two cutting edges located on the tip portion of said prongs and aligned in the X direction, and each prong having at least one locking surface extending from said prong in the Z direction; and,
   b) a retainer portion having
      (i) a base, and
      (ii) at least two columnar members attached to said base, each columnar member having an aperture to receive and retain the tip portion of a respective one of said prongs, and locking means to engage said locking surface.

2. The surgical fastener of claim 1, wherein said fastener is fabricated from a bioabsorbable material.

3. The surgical fastener of claim 2, wherein said bioabsorbable material is a polymer selected from the group consisting of homopolymers and copolymers of glycolide, lactide, caprolactone, p-dioxanone, trimethylene carbonate, and mixtures thereof.

4. The surgical fastener of claim 1, wherein said tip portion possesses at least six faces tapering to said point and at least six cutting edges.

5. The surgical fastener of claim 1, wherein said at least two cutting edges aligned in the X direction each define a raised ridge portion dividing a generally convex side of the tip into two planar polygonal surfaces.

6. The surgical fastener of claim 5, wherein said polygonal surfaces each have four sides.

7. The surgical fastener of claim 1, further including at least one guide ridge extending along the side of at least one prong in the Y direction.

8. The surgical fastener of claim 1, further including at least one raised button disposed on at least one prong.

9. A surgical fastener comprising:
   a) a generally U-shaped fastener member including
      (i) a backspan, the lengthwise extent of which defines an X direction,
      (ii) at least two substantially parallel prongs extending substantially perpendicularly from said backspan and each having a tip portion terminating in a point for piercing body tissue, the lengthwise extent of said prongs defining a Y direction, said fastener member having at least one surface defining a Z direction which is transverse to both of said X and Y directions,
      the tip portions of said prongs each having a first triangular surface facing generally outward of the fastener member in the X direction, the apex of the said first triangular surface being spaced apart from said terminal point of the prong tip by a cutting edge extending therebetween; and,
   b) a retainer portion having
      (i) a base, and
      (ii) at least two columnar members attached to said base, each columnar member having an aperture to receive and retain the tip portion of a respective one of said prongs, and locking means to engage said locking surface.

10. The surgical fastener of claim 9, wherein said fastener is fabricated from a bioabsorbable material.

11. The surgical fastener of claim 10, wherein said bioabsorbable material is a polymer selected from the group consisting of homopolymers and copolymers of glycolide, lactide, caprolactone, trimethylene carbonate, p-dioxanone, and mixtures thereof.

12. The surgical fastener of claim 9, wherein said prong tips each have at least nine cutting edges.

13. The surgical fastener of claim 12, wherein said prong tips each have at least six planar surfaces inclined at an angle from the Y direction.

* * * * *